United States Patent [19]

Shoesmith

[11] Plant 4,313

[45] Oct. 10, 1978

[54] CHRYSANTHEMUM NAMED WILDCAT

[75] Inventor: Leonard H. Shoesmith, Westfield-Woking, England

[73] Assignee: Pan-American Plant Company, West Chicago, Ill.

[21] Appl. No.: 797,492

[22] Filed: May 16, 1977

[51] Int. Cl.[2] ..... A01H 5/00
[52] U.S. Cl. ..... Plt./80
[58] Field of Search ..... Plt./76, 80–81

*Primary Examiner*—Robert E. Bagwill
*Attorney, Agent, or Firm*—Chas W. Rummler

[57] ABSTRACT

A new and distinct variety of chrysanthemum suitable for both year around greenhouse pot culture and outdoor garden use as a natural season flowering plant, characterized by its medium pink, medium sized blooms of decorative flower form, the clubby spray formation of its flowering, a relatively vigorous and upright plant habit, and a uniform 7-week photoperiodic response.

4 Drawing Figures

BACKGROUND OF THE NEW PLANT

My new chrysanthemum plant was discovered by me in 1973 as a seedling of unidentified parentage growing among random pollinated plants in my breeding grounds at Westfield-Woking, Surrey, England. Because of its attractive floral and growth characteristics, I reproduced this plant for test at my aforesaid breeding grounds by means of cuttings from the original plant and my observations and subsequent propagation of the cultivar assured me that the distinctive features of the original plant hold true from generation to generation of its asexual reproduction and appear to be firmly fixed.

This new variety of chrysanthemum is now being propagated by vegetative cuttings and grown at West Chicago, Ill., and at Cortez, Fla., with full retention of all of the novel characteristics of the original plant.

DESCRIPTION OF THE DRAWINGS

My new chrysanthemum cultivar is illustrated by the accompanying drawings, the first of which is a full color photographic print showing a potted plant of the new variety in full bloom, the colors shown being as nearly true as it is reasonably possible to obtain by conventional photographic procedures, the photograph being of a plant propagated and grown at West Chicago, Ill., and flowered in Feb. 1977.

The second drawing is a mechanical print of a photocopy of typical leaves of the new cultivar taken at several stages of maturity.

DESCRIPTION OF THE NEW PLANT

The following is a detailed description of my new chrysanthemum plant with color designations according to the R.H.S. Colour Chart published by The Royal Horticultural Society of London, England, the stated observations having been made of plants growing at West Chicago, Ill.

THE PLANT

Origin: Seedling.

Parentage: Unidentified. This plant found among random pollinated plants of a similar variety.

Classification:

*Botanic.*—*Chrysanthemum Morifolium.*

*Commercial.*—Greenhouse pot plant and outdoor garden plant.

Form: Perennial herbaceous bush.

Height: 6 to 10 inches when grown as a pot plant. 16 to 21 inches as an outdoor garden plant.

Growth: Terminal, vigorous and upright with good strength and sturdiness.

Branching: Normal under natural conditions.

Foliage: Quantity — abundant, with 4 to 8 leaves per 3 inches of stem as a pot plant.

*Leaf size.*—About 1¾ to 4½ inches long and about ⅞ to 2 inches wide. Shape: Lanceolate, lobed and deeply serrated. Color: Upper side — Yellow-Green 147A. Under side — Yellow-Green 147B. Surface texture: Canescent. Venation: Pinnately veined.

*Petioles.*—⅜ to ⅝ inch long.

THE BUD

Form: Globular.

Size:

*Diameter.*—About ¼ to 5/16 inch.

*Depth.*—About 3/16 to ⅜ inch.

Opening: The bud opens slowly.

Color:

*When phyllaries first divide.*—Yellow-Green 144A.

*When florets begin to unfurl.*—Greyed-Purple 186D.

Phyllaries: Many in number, as involucral bracts borne on the outside of the receptacle.

*Form.*—Upstanding and spear-shaped.

*Color.*—Inside surface — Yellow-Green 146A. Outside surface — Yellow-Green 146A.

*Surface texture.*—Pubescent.

Peduncle: Length — About 1¼ to 3½ inches.

*Surface texture.*—Pubescent.

*Strength.*—Erect and strong.

*Color.*—Yellow-Green 148B.

THE FLOWER

Blooming capability: This plant can be flowered the year around with photoperiod control.

*Response.*—7 weeks.

*Recommended flowering.*—March 1 to November 1 as a pot plant.

*Natural season flowering.*—About September 26 to October 9.

Blooms:

*Flower type.*—Composite and decorative.

*Size of bloom.*—Medium. Diameter $1\frac{3}{4}$ to $2\frac{1}{2}$ inches. Depth: $\frac{1}{2}$ inch.

*Shape.*—Flat.

*Borne.*—Singly, as a head of many florets carried on a receptacle, in a clubby spray formation.

*Florets.*—Quantity — Numerous. Form: Linear, with obtuse apex. Arrangement: Decorative. Texture: Medium firm. Appearance: Very slight shine. Discoloration: Considerable fade after full bloom.

| Color: | March | October | November, |
|---|---|---|---|
| Outer florets: | | | |
| Upper side - | 65A | 65A | 65A |
| Reverse - | 65D | 65B | 65B |
| Inner florets: | | | |
| Upper side - | 74D | 74D | 75B |
| Reverse - | 75D | 75C | 75D |

*General color tonality of bloom.*—65A when viewed from a distance of 6 feet.

Effect of weather: The flower is not affected by hot or wet weather.

Persistence: Florets hang on and dry.

Fragrance: Typical chrysanthemum.

Lasting quality:

*On the plant.*—3 weeks.

*As cut flower.*—Not recommended for such use.

REPRODUCTIVE ORGANS

Stamens: Number — 5. Arrangement — Syngenesious.

*Filaments.*—Length — 1/16 to $\frac{1}{8}$ inch. Color — Light Yellow.

*Pollen.*—Color — Yellow.

Pistils: Number — one for each ray and disc floret.

*Length.*—$\frac{1}{8}$ to 3/16 inch.

*Stigmas.*—Yellow in color.

Ovaries: Inferior bicarpellate.

This new chrysanthemum cultivar is particularly distinguished by the medium pink color of its medium sized decorative flower form and the clubby spray formation in which the flowers appear. There is a noticeable lack of ray florets in the center of the bloom when the plant is flowered during relatively low light conditions but the plant exhibits good performance during spring, summer and fall flowering, as a 4 to 5 inch potted plant with uniform 7-week photoperiodic response, and as a natural season garden chrysanthemum. This plant has a relatively vigorous, upright growth habit with good stem strength and abundant foliage of medium size. However, this variety requires some growth retardant treatment when grown as a potted plant and it has a susceptibility to high soluble salt conditions.

I claim:

1. The new and distinctive chrysanthemum cultivar substantially as herein shown and described, characterized by its medium pink blooms of medium size and decorative flower form, its uniform 7-week photoperiodic flowering response and good performance when grown as a spring, summer and fall potted plant, its good performance when grown as a natural season garden chrysanthemum, and its relatively vigorous upright growth habit with good stem strength and abundant, medium sized foliage.

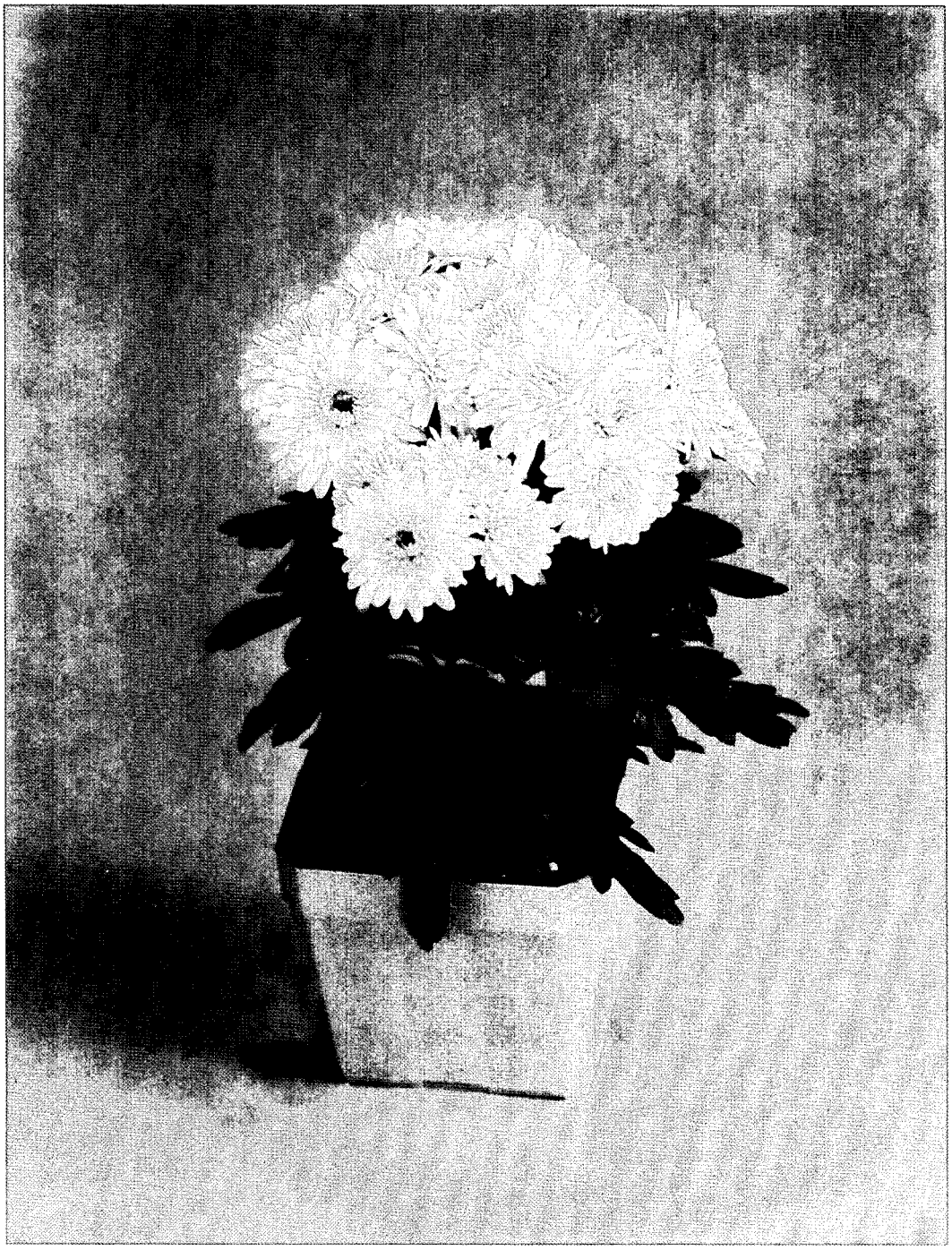

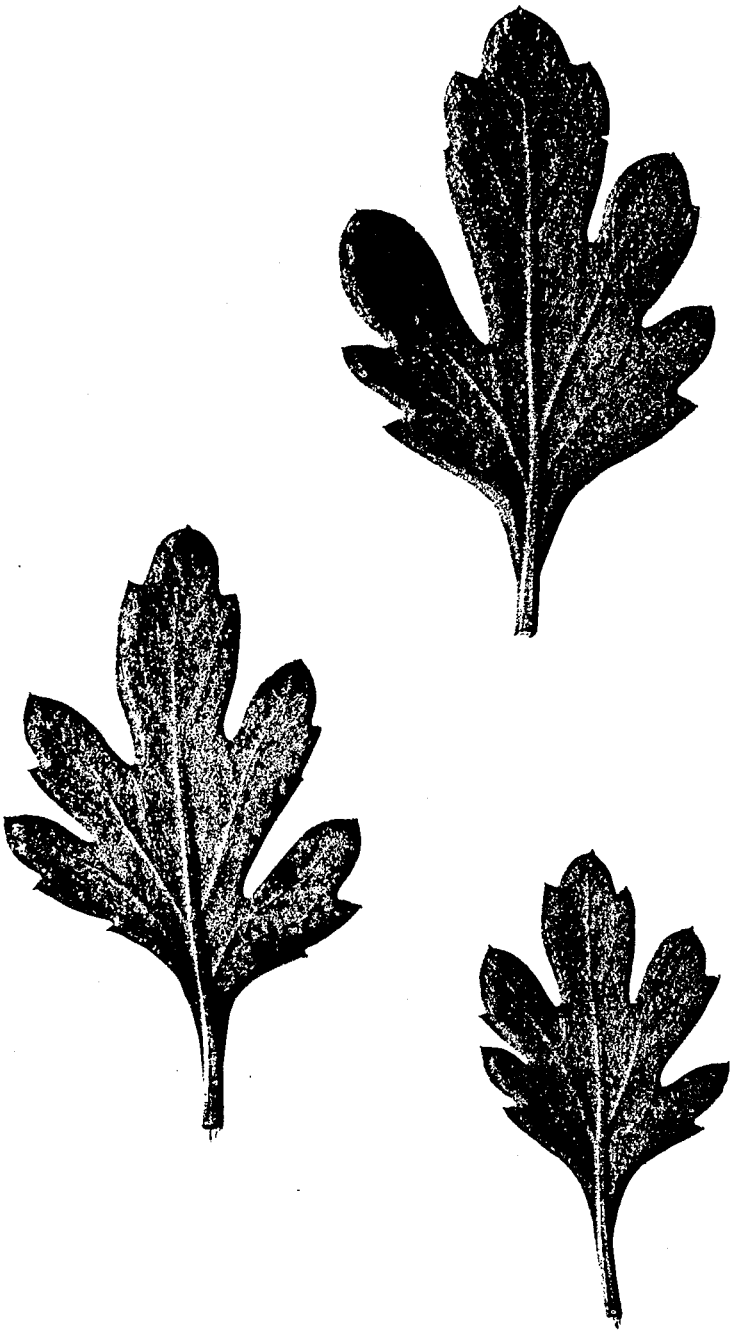

* * * * *